(12) United States Patent
Saidman et al.

(10) Patent No.: US 10,512,398 B2
(45) Date of Patent: Dec. 24, 2019

(54) PORTABLE RETINOGRAPHY DEVICE

(71) Applicants: Gabriela Roxana Saidman, Berazategui Buenos Aires (AR); Guillermo Andres Monteoliva, La Plata Buenos Aires (AR)

(72) Inventors: Gabriela Roxana Saidman, Berazategui Buenos Aires (AR); Guillermo Andres Monteoliva, La Plata Buenos Aires (AR)

( * ) Notice: Subject to any disclaimer, the term of this patent is extended or adjusted under 35 U.S.C. 154(b) by 79 days.

(21) Appl. No.: 15/834,289

(22) Filed: Dec. 7, 2017

(65) Prior Publication Data

US 2018/0153402 A1 Jun. 7, 2018

(30) Foreign Application Priority Data

Dec. 7, 2016 (AR) .............................. P20160103749

(51) Int. Cl.
| | | |
|---|---|---|
| A61B 3/12 | (2006.01) | |
| A61B 3/15 | (2006.01) | |
| A61B 3/10 | (2006.01) | |
| A61B 3/14 | (2006.01) | |
| A61B 3/00 | (2006.01) | |

(52) U.S. Cl.
CPC ............ *A61B 3/1208* (2013.01); *A61B 3/10* (2013.01); *A61B 3/1241* (2013.01); *A61B 3/14* (2013.01); *A61B 3/15* (2013.01); *A61B 3/0058* (2013.01)

(58) Field of Classification Search
CPC ....... A61B 3/1208; A61B 3/1241; A61B 3/14; A61B 3/15; A61B 3/0058
See application file for complete search history.

(56) References Cited

U.S. PATENT DOCUMENTS

| 5,576,780 | A  | * | 11/1996 | Yancey ................. A61B 3/103 351/209 |
|---|---|---|---|---|
| 9,155,466 | B2 | * | 10/2015 | Su .......................... A61B 3/125 |
| 10,188,294 | B2 | * | 1/2019 | Myung ................. A61B 3/145 |
| 2005/0174782 | A1 | * | 8/2005 | Chapman ............... F21L 4/027 362/319 |
| 2009/0093274 | A1 | * | 4/2009 | Yamamoto ......... G02B 13/0015 455/566 |
| 2012/0320340 | A1 | * | 12/2012 | Coleman, III .......... A61B 3/14 351/208 |
| 2013/0083185 | A1 | * | 4/2013 | Coleman, III .......... A61B 3/12 348/78 |
| 2013/0128223 | A1 | * | 5/2013 | Wood .................. A61B 5/0077 351/206 |
| 2016/0051142 | A1 | * | 2/2016 | Howes .................... A61B 3/14 351/245 |
| 2016/0296112 | A1 | * | 10/2016 | Fletcher .................. A61B 3/14 |
| 2016/0338587 | A1 | * | 11/2016 | Gupta ................. A61B 3/1208 |
| 2017/0035294 | A1 | * | 2/2017 | Massie .................. A61B 3/102 |
| 2017/0303857 | A1 | * | 10/2017 | Perkins ................. A61B 1/227 |

(Continued)

*Primary Examiner* — William R Alexander
*Assistant Examiner* — Ephrem Z Mebrahtu
(74) *Attorney, Agent, or Firm* — Norris McLaughlin, P.A.

(57) ABSTRACT

A manual image-capturing device for the registration of low-cost ophthalmological images, accessible to those countries and places that do not have access to conventional high-cost devices, wherein the device of the invention allows taking and recording images of the retina using smart mobile devices such as for example smart phones, also allowing live transmission of the ophthalmological examination.

10 Claims, 5 Drawing Sheets

(56) References Cited

U.S. PATENT DOCUMENTS

2018/0092534 A1* 4/2018 Nabhan .................... A61B 3/14
2018/0116509 A1* 5/2018 Myung .................... A61B 3/10
2019/0117064 A1* 4/2019 Fletcher ............... H04N 5/2354

* cited by examiner

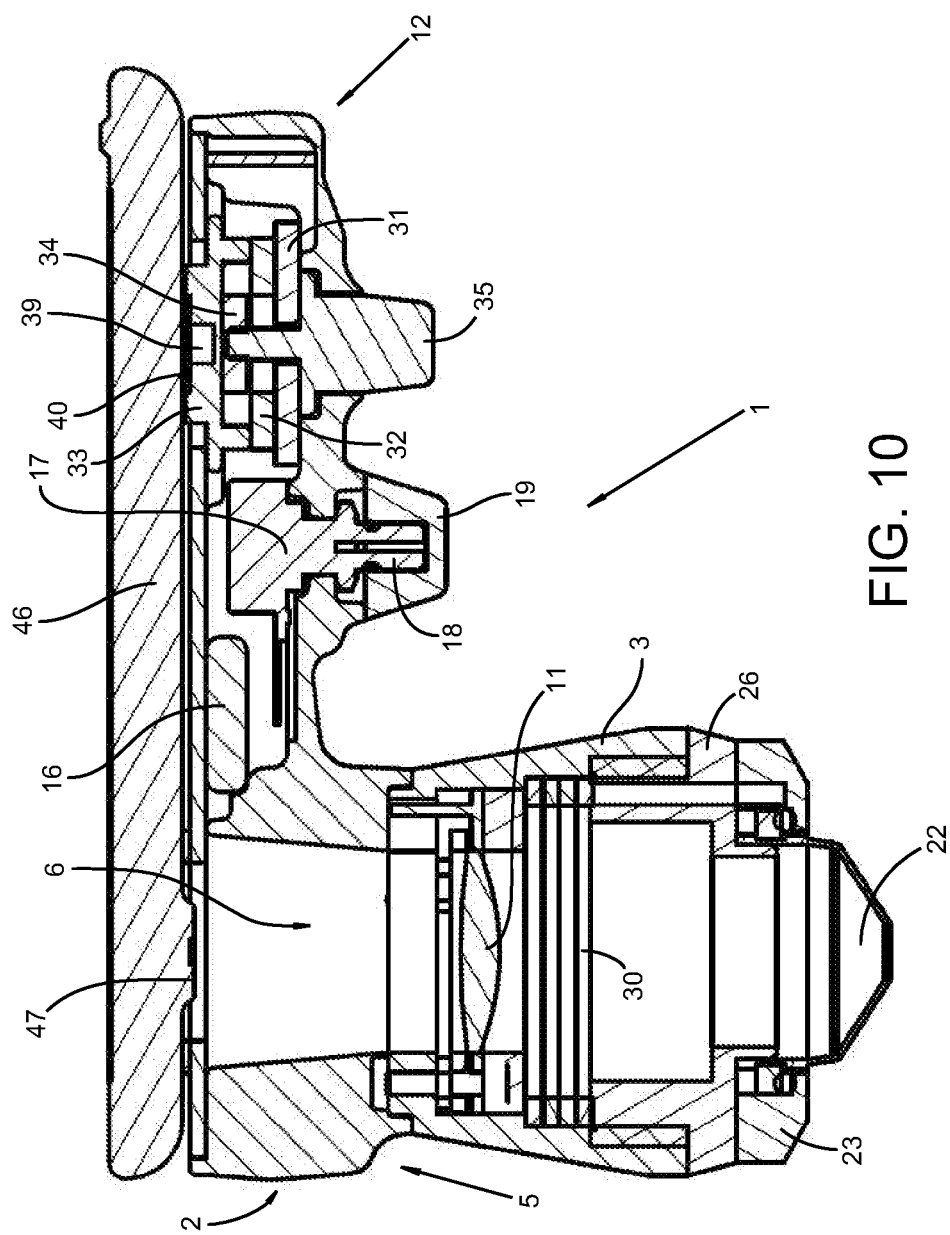
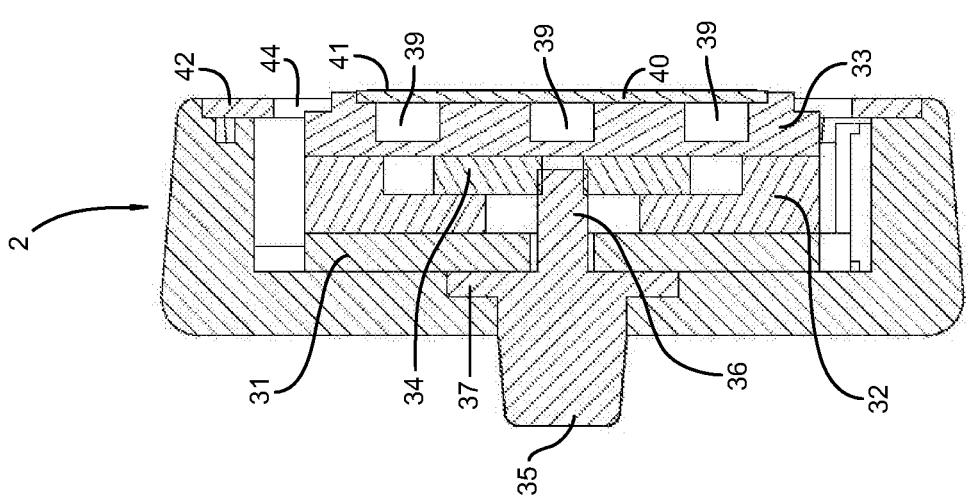
FIG. 10
FIG. 9

PORTABLE RETINOGRAPHY DEVICE

BACKGROUND OF THE INVENTION

1. Field of the Invention

The present invention relates to the field of devices, apparatus and arrangements used in the field of medicine and more particularly it refers to a manual device that allows carrying out visual examinations on a part of a patient under study, and even more particularly refers to a device on which a wide-angle camera or cell phone can be mounted, more precisely a smart phone, popularly known as "Smartphones", capable of taking images, processing and sending them at will, or of transmitting live to other places or devices the images that are recorded during the ophthalmological examination, wherein said device is inexpensive and can be used in those countries and places that are not in good economic conditions.

2. Description of the Prior Art

Before entering into the description of the devices and systems known in the art and used for the aid of ophthalmological examinations, it is convenient to make references to technical concepts that will help to better understand the object and content of the invention.

The study of visual diseases requires, at least in the first steps, the visual examination of the eyes through devices that allow the medical professional to observe them in detail, for example, through the use of lenses or glasses that magnify the ocular sphere. These magnifiers are very well known in the art and are used in combination with other lighting devices, capable of emitting beams of light that fall on the eyeball and return, through the lenses, enlarged images that allow the professional to evaluate the case.

These visual examinations are done, among the known techniques, by means of Indirect Ophthalmoscopy in which the so-called Indirect Ophthalmoscope is used, which is a device for medical use that uses a light, source directed to the interior of the patient's eye by means of an adjustable mirror, whereby the reflected light is gathered by a condensing lens, to form an inverted real image of the retina. It provides a high intensity illumination, which allows performing the fundoscopy even through turbid optical media, stereoscopic vision and a wide visual field, as well as a dynamic assessment of the vitreoretinal pathology.

In summary, indirect binocular ophthalmoscopy uses prisms and coaxial light that allow seeing the retina with a magnifying glass, the optic nerve and the vitreous body in binocular form to evaluate all types of diseases of the ocular fundus. Due to its powerful light it also allows evaluating patients with cataract or opaque media.

The technique of indirect binocular ophthalmoscopy is the most used by ophthalmologists is routine retinal examinations, since if performed with an ordered sequence, it allows reviewing the ocular fundus in its 360° examined by parts, in clock hours, according to the technique. There is the standard gold technique used by ophthalmologists and retinologists.

There are also other techniques that are used to visualize the ocular fundus with the help of the slit lamp which is as ophthalmological device that consists of a binocular viewer and a lighting system in a lateral column, using special contact and non-contact magnifying glasses, which are placed on the patient under examination positioned on said examination lamp. In this examination, the binocular vision system and the illumination of the slit lamp are used, to enter light to the eye that is reflected in the retina and returns to the binocular viewer. Non-contact and contact lenses can be used for this examination.

The technique with slit lamp is called biomicroscopy. And the fundoscopy made with slit lamp is called biomicroscopy with contact lens, or with non-contact lens, depending on the lens that is used.

Contact lenses of the retinal examination with slit lamp are widely known, so they are not going to be described, and they can reach wider areas of the eye, using mirrors or wide-angle optical systems that allow visualizing a smaller image and wider area of the retina. Generally these lenses are used to visualize the retina and evaluate laser treatments, and to perform laser procedures, once a review with the indirect binocular ophthalmoscope has been previously performed. The wide-angle contact lenses for ocular fundus biomicroscopy with slit lamp allow visualizing wide areas of the retina according to the optical system of each lens; there are several models and marks, with up to 160° angular among the most used. And they are used to perform laser treatment of the retina, visualizing the entire area, with slit lamp biomicroscopy.

Although there are digital wide-angle retinal image recording systems, these are very costly, so not all countries and places can have access to them.

Given the current state of the art and its concerns, it would be very convenient to have a new technology that allows countries that can not afford high-cost conventional digital retinal image recording systems, to access the use of a lower-cost device and that in turn, be able to take advantage of the use of smart phones for the registration of images in ophthalmological examinations and, more particularly for the registration of retinal images, also allowing processing and arranging those images in telecommunication networks in real time or for registration in databases.

SUMMARY OF THE INVENTION

It is therefore an object of the present invention to provide a new low-cost device for the registration of ophthalmological images, and more particularly images of the retina of a patient, by the use of a smart phone or a wide-angle camera.

It is still another object of the present invention to provide a low-cost and easily accessible device in those countries and places that can not afford a conventional high-cost retinal image capture system.

It is still another object of the present invention to provide a device that allows live transmission or "streaming" of the ophthalmological examination.

It is also another object of the present invention to provide a device that can be adapted to different magnifying glasses or lenses in a practical, quick and easy manner.

It is still another object of the present invention to provide a device for the live transmission of the ophthalmological examination, allowing telemedicine sessions in remote places of the country, in serious cases.

It is also another object of the present invention to provide a device that achieves wide-angle retinal images in an economical, efficient and safe way, taking advantage of a technology available to any individual.

It is also another object of the invention, through light input and output filters of retinal images that it possesses, to provide a device that achieves to perform angiography studies of the retina, and auto fluorescence studies of some layers of the retina and evaluation of retinal layers, through the joint or separate use of these filters that the device possesses.

It is still another object of the present invention to provide a device to be used in telemedicine and extendible to all infants and children under 3 years old with other diseases.

It is yet another object of the present invention to provide a manual device for capturing images for recording ophthalmological images, comprising at least one main body comprising an upper section provided with a conical through hole and an upper support base on which an illuminating ring and a lens are mounted, a lower section provided with an inner housing, and a rear cover; at least one conical lens body that is removably mounted on said upper section of the main body and operatively connected to said illuminating ring and to the lens, said conical lens body having at least one contact lens; and at least one support means which is arranged within the inner housing of the lower section of the main body and which retains an image capturing device.

BRIEF DESCRIPTION OF THE DRAWINGS

For greater clarity and understanding of the object of the present invention, it has been illustrated in several figures, in which the invention has been represented in one of the preferred embodiments, all by way of example, wherein:

FIG. 9 shows a sectional view of section B-B of FIG. 7; and

FIG. 10 shows a cross-sectional view of the device of the present invention, wherein there can be viewed a smart cellular telephone that is mounted on said device according to a use mode, but not limiting, of the present invention.

DESCRIPTION OF THE PREFERRED EMBODIMENTS

Figure 1:
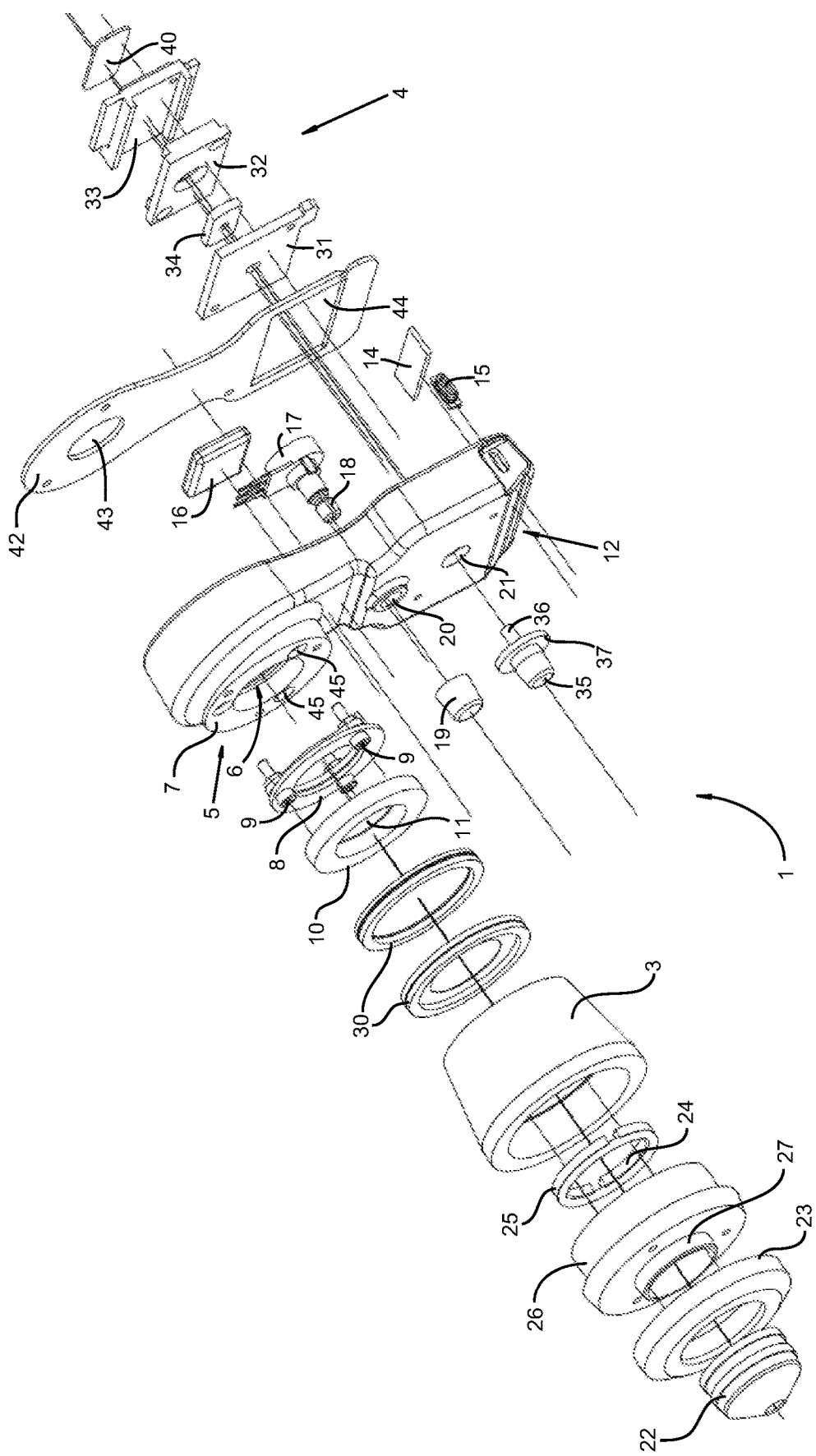
FIG. 1 shows a perspective and exploded view of the device according to the present invention.
Figure 2:
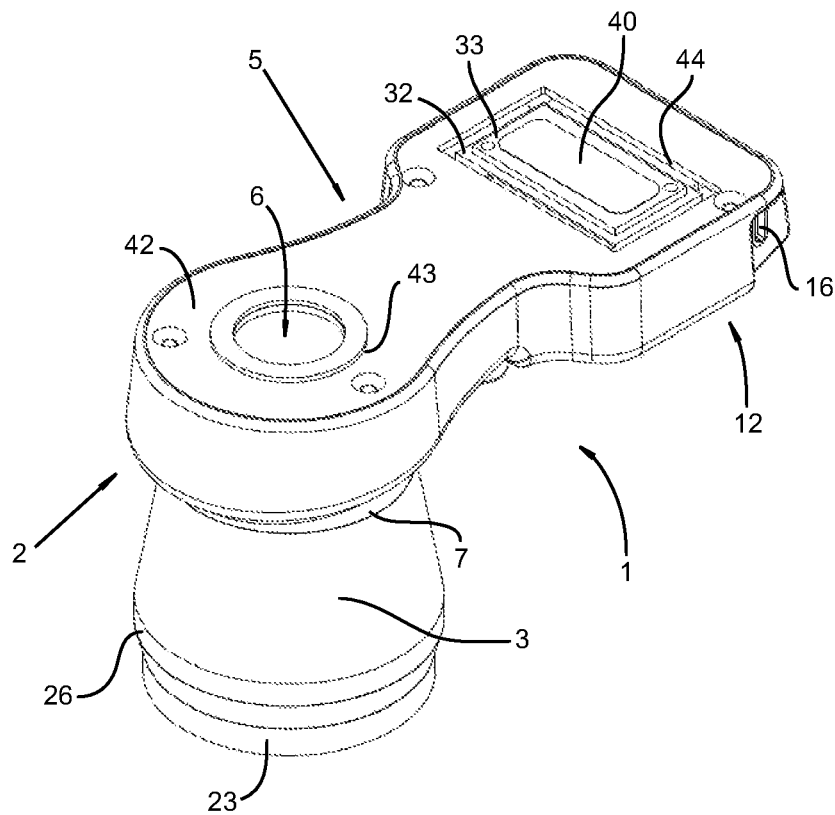
FIG. 2 shows a perspective view taken from above and one side of the device of the invention.
Figure 3:
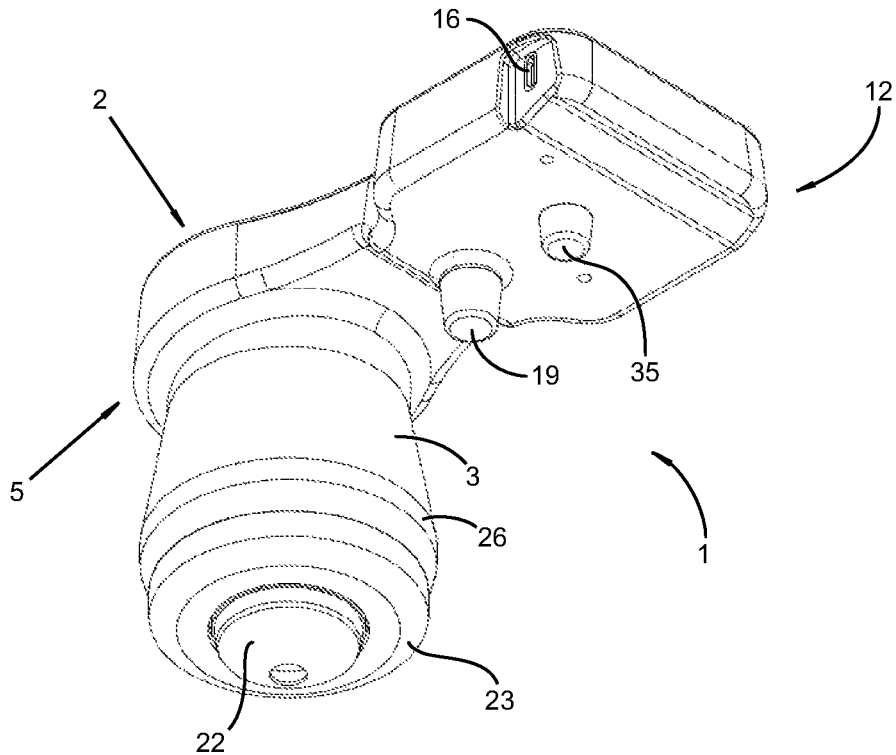
FIG. 3 shows a perspective view taken from below and one side of the device according to the present invention.
Figure 4:
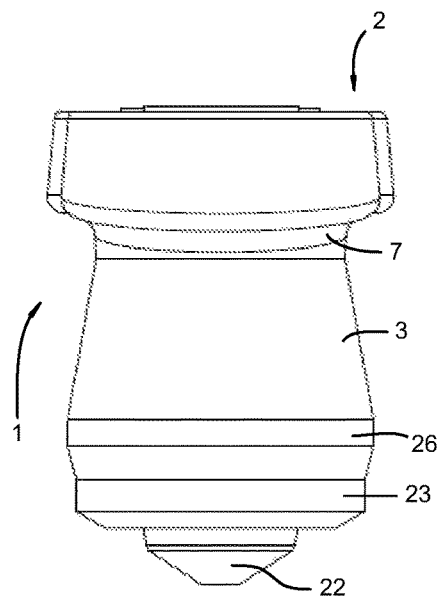
FIG. 4 shows a front view of the device of the present invention.
Figure 5:
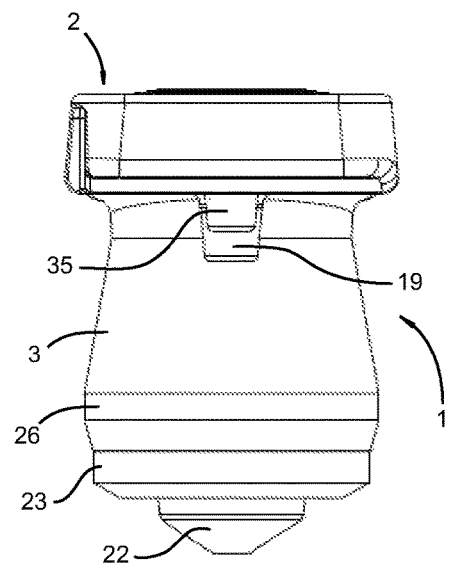
FIG. 5 shows a rear view of the device of the present invention.
Figure 6:
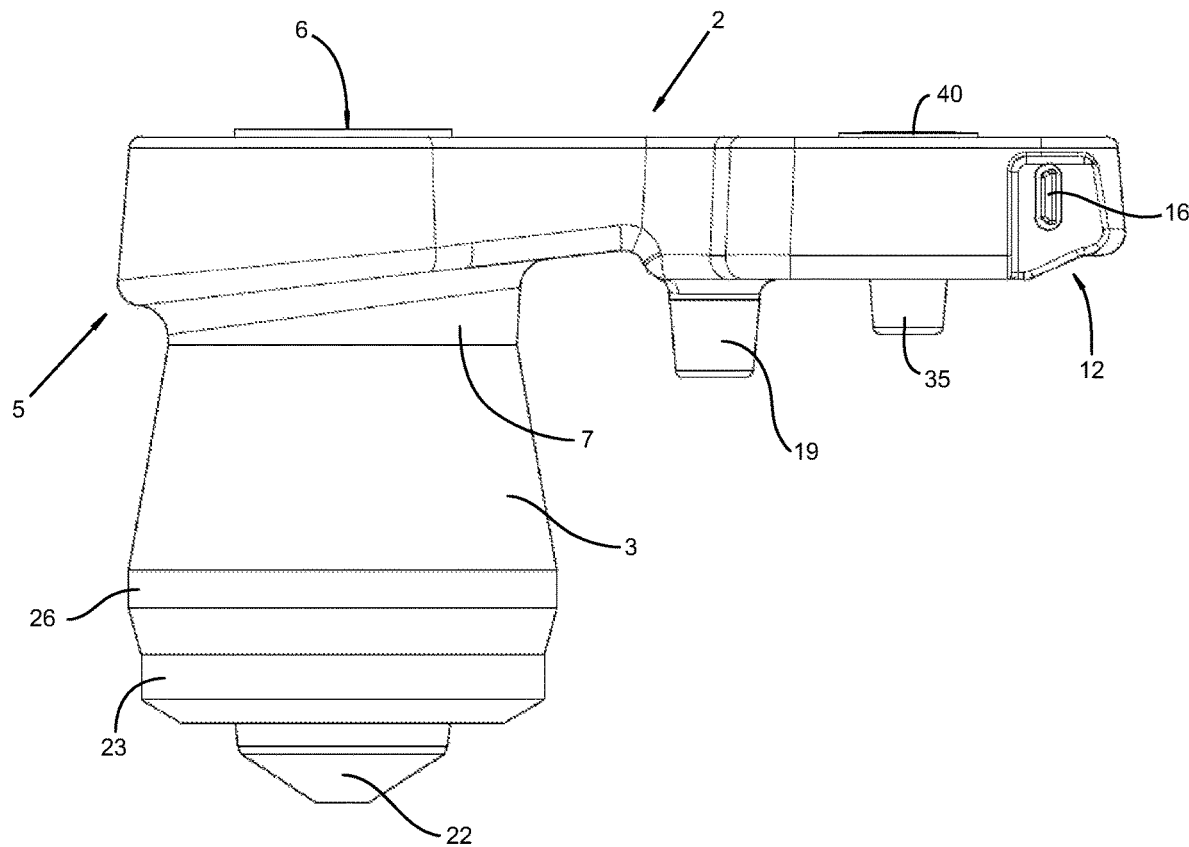
FIG. 6 shows a side view of the device of the present invention.
Figure 7:
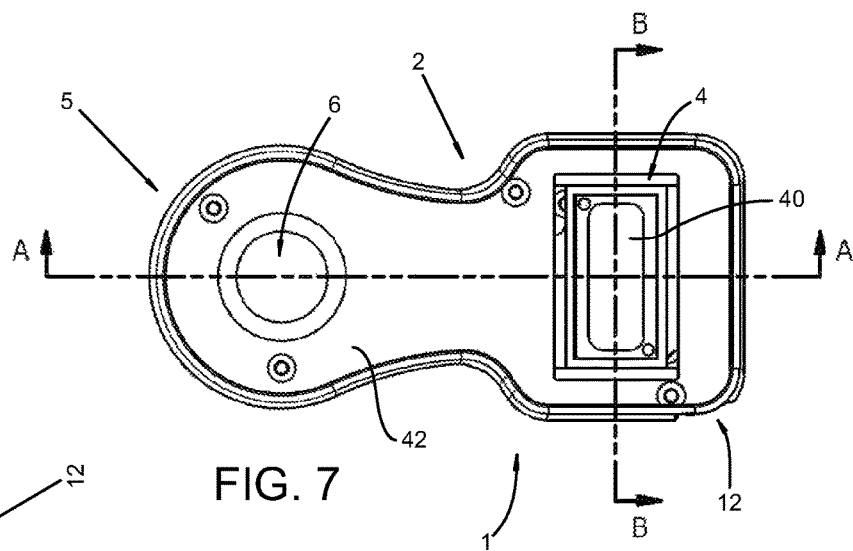
FIG. 7 shows a plan view of the device of the present invention, wherein a section cut A-A and a section cut B-B are indicated.
Figure 8:
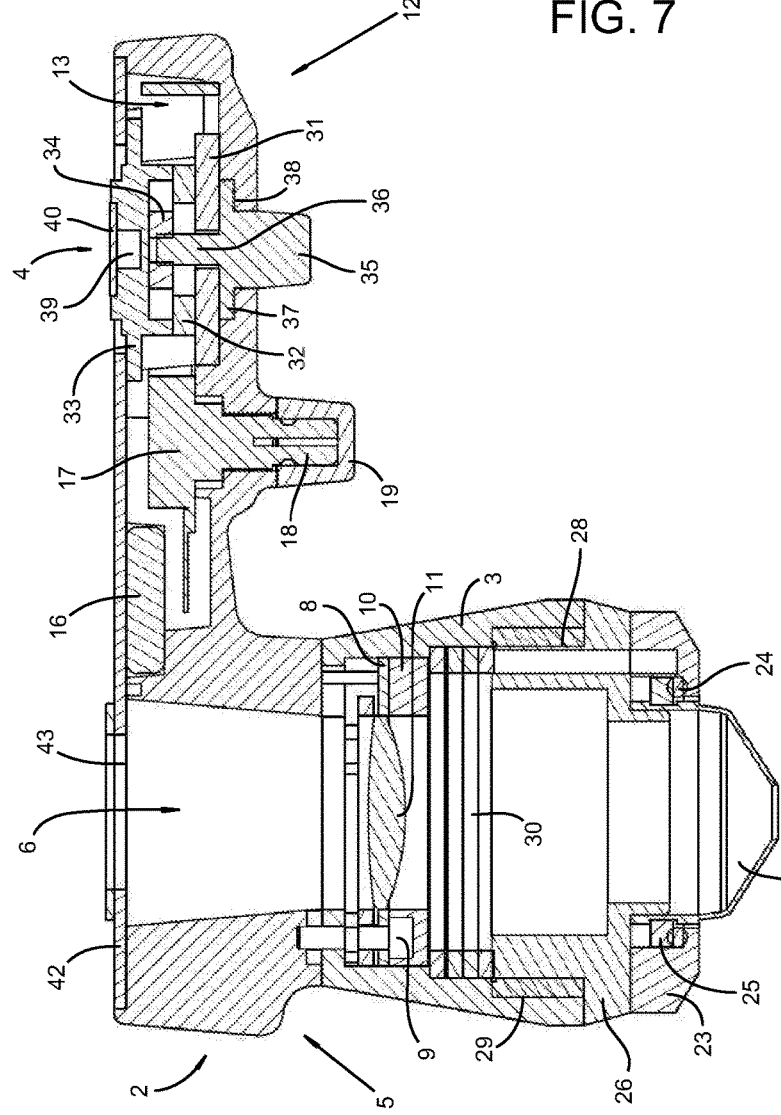
FIG. 8 shows a sectional view of section A-A of FIG. 7.

Referring now to FIGS. 1 to 10, it is seen that the invention consists of a new manual image capturing device s for recording ophthalmological images, which is indicated by general reference and which comprises a main body 2 which receives a conical lens body 3 and a support means 4. Wherein, said main body 2 comprises an upper section 5 provided with a conical through hole 6 and an upper support base 7 provided with a plurality of holes 45 and in which a ring-shaped plate 8 is mounted which has a plurality of white LED lights 9 and receives an illuminating ring 10 which is a translucent encapsulation and a lens 11. It is emphasized that said translucent encapsulation is an encapsulation which diffuses white LED lights 9 that are partially housed in said holes 45 and which are fixed by respective screws, while said lens 11 is a biconvex lens having at least twice magnification or ×2 that serves to enlarge displayed images without the use of the digital zoom of an image capturing device.

Likewise, said main body 2 has a lower section 12 provided with an inner housing 13 in which said support means 4 is housed which will be described below. On the other hand, the main body 2 has a circuit board 14 which is operatively connected to said white LED lights 9, at least one micro USB charging connector 15 for charging a battery 16, and a potentiometer 17 with knob 18 and grip cap 19 which is connected to said circuit board 14 to jointly allow the regulation of the light intensity of the LED lights 9. As can be seen in FIG. 1, said main body 2 is provided with a pair of holes 20 and 21, wherein the knob 18 of potentiometer 17 passes through the hole 20.

With regard to the conical lens body 3, it is removably mounted on said upper section 5 of the main body 2. Wherein, said conical lens body 3 comprises at least one contact lens 22 for eye contact which is mounted on a lens support 23 by means of at least one O-ring or joint ring 24 which in turn is mounted on an O-ring fixing part 25. The assembly consisting of the lens 22-lens support 23-O-ring 24-O-ring fixing part 25, is connected to/mounted on a lens fixing means 26 which has a lip 27 on which the base of the lens 22 rests, wherein the o-ring or joint ring 24 retains said base 22 and lip 27 on the outside for being fixed. Likewise, the lens fixing means 26 is threadedly connected to said conical lens body 3, said lens fixing means being provided with a male thread 28, while the conical lens body 3 has a female thread 29. However, this does not imply that the invention is limited to said thread arrangement, but that the arrangement of threads can be reversed without any inconvenience. It is emphasized that, as said lens fixing means 26 has a male thread, this considerably facilitates the exchange of the whole assembly in case of wanting to change the lens. In turn, the conical lens body 3 can accommodate, if necessary, colored acetate filters 30 to cause the white light to transform into color and to filter ribs and details so that they are better seen with said color. These filters act for the evaluation, if necessary, of specific layers of the retina, a topic studied and known by ophthalmologists in their daily practice, and as filters that allow excitatory light to pass with wavelength below 510 nm or block light with more than 510 nm, for performing retinal angiography with fluorescein, a common technique in ophthalmology.

For its part, said support means 4 is arranged inside the inner housing 13 of the lower section 12 of the main body 2 and comprises a position adjusting base 31 that receives a linear guide base 32 which is operatively connected to a linear guide 33. Between said linear guide base 32 and linear guide 33 there is provided at least one orbitally slidable regulator 34 which is operatively connected to an adjustment knob 35 with screw 36 arranged in a portion of the lower section 12 of the main body 2 opposite to that in which the support means 4 is housed. It is emphasized that said adjustment knob 35 has a circumferential flap 37 that rotatively fits inside a receptacle 38 made in the inner housing 13 of the main body 2. Likewise, a portion of the adjustment knob 35 passes through the hole 21 made in the main body 2. On the other hand, said linear guide 33 accommodates a plurality of neodymium magnets 39 which are retained by a linear guide cover 40 formed of zinc-plated iron sheet, said linear guide cover 40 having a self-adhesive means 41 which is in contact with an image capturing device, so that it sticks thereto, and that when desired, the device can be removed with a simple pull in order to separate it from magnets 39.

It is noted that a rear cover 42 provided with an upper hole 43 and a lower hole 44, allows hiding those parts that are housed inside the main body 2. Likewise, said support means 4 allows orbitally adjusting an image capturing device 46, such as a smart cell phone, in position, and thus be able to align the camera or rear viewer 47 of the phone with the lenses, as best illustrated in FIG. 10. Wherein, said regulator 34 slides orbitally and serves as the nut of the adjustment knob 35. With regard to the linear guide base 32 and linear guide 33, they allow sliding in lateral form. On the other hand, the neodymium magnets 39 magnetically hold and retain the image capturing device 46, with the aid of the adhesive 41 provided in the cover 40.

In this way, a device is obtained that allows carrying an image capturing device, such as a smart cellular telephone, in order to align the rear camera thereof, with an arrangement of lenses and filters, for the ophthalmological inspection. Also, one can visualize live on the screen of the smartphone, allowing the capture and recording of ophthalmological images. By presenting white led lights, the device allows illuminating the lens from inside. It should be noted that said image capturing device can be a smart cell phone which can be connected to a display screen via a WiFi connection, Bluetooth or HDMI cable.

Thus, it is possible to take or record images of the retina, as well as, transmit live or by "streaming" the ophthalmological examination to be performed on a patient. Live transmission or "streaming" of the examination allows a better training of future professionals or professionals, as well as the possibility of live teleconferences in Congresses that are held worldwide.

It should be noted that the device of the present invention operates with a magnifying glass that allows seeing the retina, optic nerve and vitreous body, which is well known and used in the field of art and that for such reasons, we will not go into descriptive details about the structural configuration thereof. Wherein, it is known that the lower the dioptric power of the magnifying glass is, the greater the image and smaller the area are and vice versa.

It is highlighted that, if each working team of a network has a registration method, serious cases can be reported and consultancies can be made. Retinopathy of prematurity has areas with difficulties in research and consultancies and for these reasons; it is convenient to use the device of the invention. In turn, the device of the invention is useful for the Prevention of Blindness due to retinopathy of prematurity and serious retinal diseases such as tumors, for example retinoblastoma, so its usefulness has a great positive impact on the health of children in growth and development. Furthermore, it helps to prevent serious forms of eye diseases such as Retinopathy of prematurity, ocular tumors, tumors of the nervous system, evaluation in severe and traumatized inpatients.

In an application example, the invention can be used in cases of ROP lesion, peripheral retinopathy of prematurity, being important for late or regression ROP where evolution can be recorded and compared. The control of a premature baby is performed, in which the professional rotates the eyeball and controls the evolution of Retinopathy of prematurity grade 1 in zone III (peripheral), as it is usually done all over the world with indirect binocular ophthalmology. There is a white line, line of demarcation of the ROP 1, which in the controls of the baby will be erased as the vessels grow towards the periphery. The registry allows you to compare images, explain to parents about what their child has in real time, improving adherence to follow-up controls and the doctor-patient relationship.

Although, a device has been described to be used in ophthalmology, it should be noted that it can be used, through the use and adaptation of the accessory, with other wide-angle magnifying glasses used in general ophthalmology and prevention of other pathologies such as diabetes, maculopathy, arteriopathies, tumors, neuro-ophthalmology, trauma, retinal detachment, various diseases, inherited retinal degenerations, congenital malformations, etc.

In alternative and illustrative form, the invention may be connected to or use a registration system or mobile application, for patient safety and better management of images. The mobile application allows the secure registration of data (with the use of bar codes or IQ); Authorization of family or patient for the Registry attached to the study (through some system of scanning of the signed authorization, integrated in the APP) record of epidemiological data (that can be compatible with data to be sent to Epidemiology Centers); Registration of images and their edition; storage in device and subsequent sending to backup system; or data encryption (to secure the identity of images and patient).

By way of example, but not being limited for the invention, professional mobile applications (App) of video and edition with Smartphone can be used. For example, the mobile application FILMIC Pro, already available for IOS and Android systems, allows pre-setting high-resolution shooting parameters, e.g. 4K, Slow, etc., already known in these phones. But when the device, helmet and arm are positioned in a predetermined distance of work, you can do studies for setting different colors of retina, according to the amount of pigment thereof, as well as presetting the focus, amplitude, white balance, etc., allowing an easier use, a better learning curve and better performance (performance) in the registry. Since usually the factory default video mode is used, and often it takes time to accommodate the image or there are images "burned" due to excess of light etc. (for example a calcified tumor lesion of retinoblastoma that "burns image" by reflectivity of flash led light video due to calcium, can be set with low gain of white balance, etc.).

Thus, the invention allows us to review studies as many times as one wants due to doubts about clinical aspects of injuries and parts of the ocular fundus, just by reviewing the video. In a running, paused way, upon detecting the lesion, one can run back and forth to observe light reflectivity on ocular tissues. Furthermore, there can be detected other additional lesions that can be overlooked in an OBI examination because of paying more attention to the main lesion, which increases the importance in a diagnosis. Also in this sense, being able to transmit to a monitor or Smart TV in real time, makes it possible for the case to be evaluated at that moment by several observers in a work team with a single observation (greater number of observers) becoming in complex cases an athenaeum in real time. Likewise, "streaming" system of Smartphones can be added for use in Telemedicine in e-health networks (consultancies in remote regions for serious cases, with Base Hospitals). The invention is an excellent complement for networks, with informed consent in severe cases, since it makes it possible to register lesions, even the very peripheral ones, and favoring the adherence of patient and family to attend follow-up controls of investigations or post-treatment controls, through the use of comparative images.

It should be noted that, the device of the invention is a low cost device compared to the conventional high-cost devices used today, wherein those countries or places that did not have access to them before, can now use the present invention, as a technology that makes it possible to best use current devices (for example, smart cellular telephones).

Furthermore, the device of the present invention can operate in conjunction with other devices placed in front of the eyes to observe 3D images, being placed without any inconvenience.

We claim:

1. Portable retinography device for taking and recording ophthalmological images, the device comprising:
    at least one main body comprising an upper section provided with a conical through hole and an upper support base on which an illuminating ring and a lens are mounted, a lower section provided with an inner housing, and a rear cover;
    at least one conical lens body that is removably mounted in said upper section of the main body and operatively connected to said illuminating ring and to the lens, said conical lens body having at least one contact lens;
    at least one support means which is arranged within the inner housing of the lower section of the main body and which retains an image capturing device,
    wherein said support means comprises a position regulating base that receives a linear guide base which is operatively connected to a linear guide, and
    at least one slidable regulator provided between said linear guide base and linear guide, with the slidable regulator being connected to a screw adjustment knob disposed in a portion of the lower section of the main body.

2. The device of claim 1, further comprising a ring-shaped plate mounted on said upper support base, which has a plurality of LED lights and which receives said light ring which is a translucent encapsulation in which said lens is retained.

3. The device of claim 2, wherein said lens is a biconvex lens having at least two times magnification or ×2.

4. The device of claim 2, wherein said main body further presents a circuit board that is operatively connected to said LED lights, at least one charging connector connected to a battery and a potentiometer with knob which is connected to said circuit board.

5. The device of claim 1, wherein said contact lens is mounted on a lens holder by means of at least one O-ring or joint ring mounted on an O-ring fixing part, the assembly consisting of the contact lens being—lens holder-O-ring-O-ring fixing part, is mounted on a lens fixing means which has a lip on which a base of the contact lens rests, said lip and base of the contact lens being retained by means of said O-ring or joint ring.

6. The device of claim 1, wherein said conical lens body further houses at least one colored acetate filter.

7. The device of claim 1, wherein said linear guide houses a plurality of neodymium magnets which are retained by a linear guide cover constituted of zinc-plated iron sheet, said linear guide cover having a self-adhesive means which is in contact with said image capturing device.

8. The device of claim 7, wherein said image capturing device is a smart cellular telephone.

9. The device of claim 8, wherein said image capturing device is connected to a display screen via a WiFi or Bluetooth connection.

10. The device of claim 8, wherein said image capturing device is connected to a display screen by an HDMI cable.

* * * * *